United States Patent [19]

Hulsker et al.

[11] Patent Number: 5,130,157
[45] Date of Patent: Jul. 14, 1992

[54] PROCESS FOR CONCENTRATING LACTONES

[75] Inventors: Franciscus H. Hulsker, Oosterhout; Koene de Jong, Epe; Hessel Turksma, Delft, all of Netherlands

[73] Assignee: Van den Bergh Foods Co., Division of Conopco, Inc., Lisle, Ill.

[21] Appl. No.: 646,506

[22] Filed: Jan. 23, 1991

Related U.S. Application Data

[63] Continuation of Ser. No. 283,648, Dec. 13, 1988, abandoned.

[30] Foreign Application Priority Data

Dec. 15, 1987 [NL] Netherlands .......................... 8703026

[51] Int. Cl.$^5$ ............................................. A23L 1/226
[52] U.S. Cl. .................................... 549/295; 426/538; 426/650; 426/492; 203/41; 203/81; 549/273; 549/328; 554/175; 554/193
[58] Field of Search ............... 426/492, 603, 534, 538, 426/650; 260/420, 428; 203/81, 41; 549/273, 295, 328

[56] References Cited

U.S. PATENT DOCUMENTS

| | | | |
|---|---|---|---|
| 1,909,605 | 5/1933 | Belden | 203/41 |
| 2,819,169 | 1/1958 | Boldingh | |
| 2,903,364 | 9/1959 | Wode | |
| 3,981,892 | 9/1976 | Skorianetz | 426/536 |
| 4,113,752 | 9/1978 | Watanabe | 260/428 |
| 4,154,750 | 5/1979 | Moore | 260/428 |
| 4,156,688 | 5/1979 | Zosel | 260/428 |
| 4,271,076 | 6/1981 | Becker | 426/536 |
| 4,394,221 | 7/1983 | Stage | 260/428 |
| 4,465,695 | 8/1984 | Mookherjee | 426/538 |
| 4,504,503 | 3/1985 | Biernoth | 426/312 |
| 4,560,442 | 12/1985 | Jain | 203/99 |
| 4,629,534 | 12/1986 | Ezell | 203/99 |
| 4,767,869 | 8/1988 | Harrison | 203/81 |
| 4,851,085 | 7/1989 | De Thomas | 203/35 |
| 4,863,570 | 9/1989 | Wijn | 203/98 |
| 4,927,652 | 5/1990 | Haring | 426/330.6 |

FOREIGN PATENT DOCUMENTS

| | | | |
|---|---|---|---|
| 578288 | 6/1959 | Canada | 426/603 |
| 586782 | 11/1959 | Canada | 426/603 |
| 51-109908 | 9/1976 | Japan | 260/428 |
| 56-22722 | 3/1981 | Japan | 426/534 |
| 58-146252 | 8/1983 | Japan | 426/603 |
| 1423004 | 1/1976 | United Kingdom | 426/534 |

OTHER PUBLICATIONS

Yong-Quan, 1987, Kepue Shiyan 5:211-215 (translation).
JOACS 42 (1965) 847-861.
J. Dairy Res. 43 (1976) 469-477.
JOACS 47 (1970) 299-302.
Chemical Abstracts 108 No. 22 188814u.

Primary Examiner—Carolyn Paden
Attorney, Agent, or Firm—Rimma Mitelman

[57] ABSTRACT

The present invention relates to a process for obtaining an aroma concentrate that is enriched in lactones. The present invention is particularly concerned with a process for concentrating lactones from a distillate obtained by the distillative deacidification of a fat composition rich in lauric acid residues, said distillate containing at least 0.1 wt. % of lactones having 6–20 carbon atoms, by subjecting the distillate or a fraction thereof to a fractional distillation so as to obtain a fraction containing at least 1 wt. % of lactones having 6–20 carbon atoms.

The present invention offers a commercially and technically attractive route for obtaining natural lactones.

Other aspects of the present invention are a lactone concentrate obtainable by the above process, the use of such a concentrate for flavoring food products and to food products flavored by such a lactone concentrate.

8 Claims, 1 Drawing Sheet

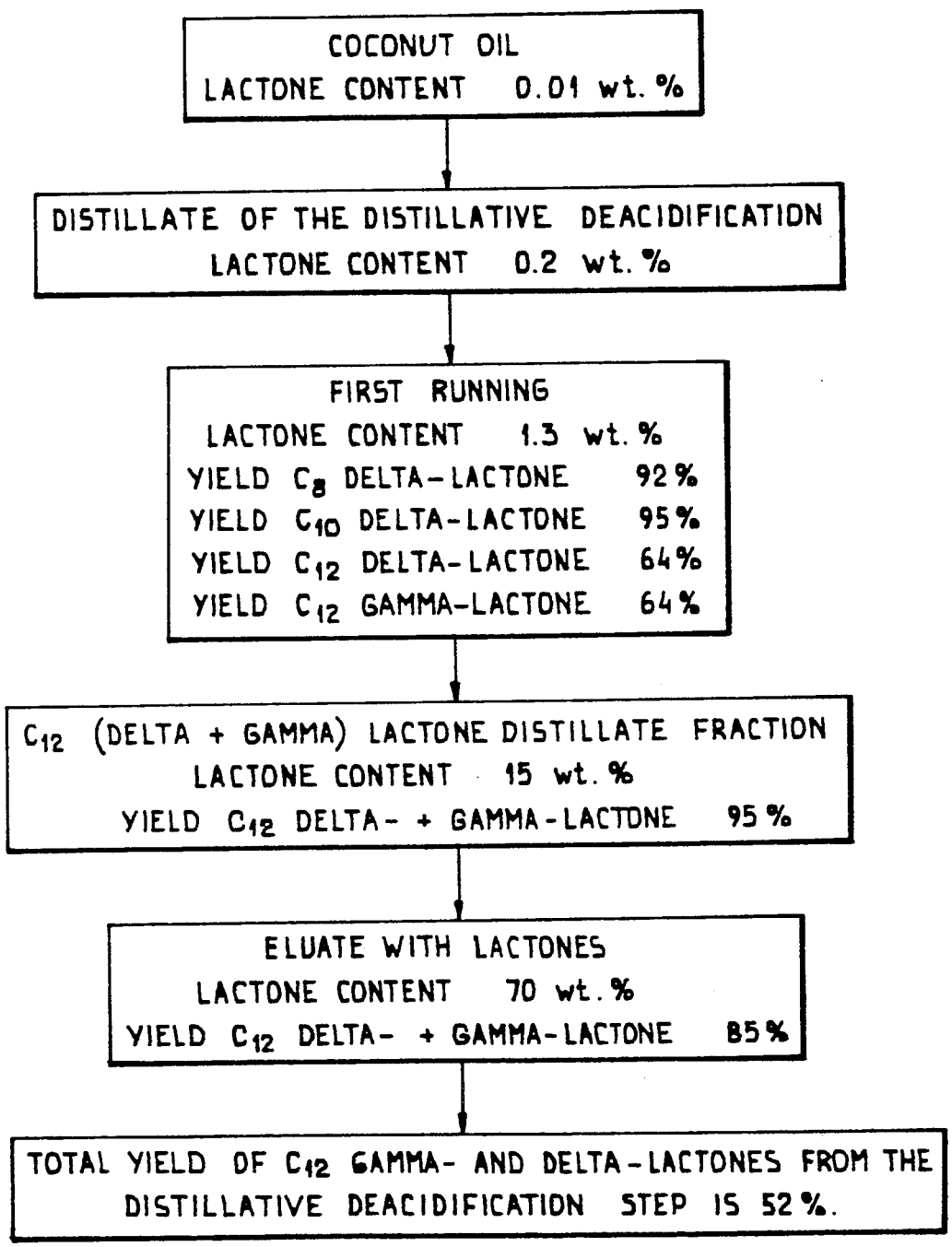

PROCESS FOR CONCENTRATING LACTONES

This is a continuation application of Ser. No. 283,648, filed Dec. 13, 1988, now abandoned.

BACKGROUND OF THE INVENTION

The present invention relates to a process for obtaining an aroma concentrate that is enriched in lactones.

Aliphatic lactones, particularly internal esters of 4-, 5- or 6-hydroxyalkanoic acids having 6-20 carbon atoms comprise compounds of which it is known that they are responsible for part of the specific odour and taste of butter. They occur in butter in a concentration of 0.1-35 ppm (J.A.O.C.S. 42 (1965) 857-861 and J. Dairy Res. 43 (1976) 469-474).

For use in all kinds of foodstuffs the above-mentioned lactones are highly valued aroma compounds. That is why, already for some considerable time, lactones are also being prepared via chemical synthesis, with racemic mixtures being obtained.

Although attention has already been paid for a considerable time to the preparation of aroma compounds in a natural manner, and despite the fact that various analytical methods of identifying and isolating lactones have been developed on laboratory scale, up to now there is still no technically and commercially acceptable method known for the large-scale concentration of lactones from natural products.

In J.A.O.C.S. 47 (1970), 299-302 an analytical method for isolating lactones from materials like milk fats of cow and goat and from the crude fats of coconut, palm kernel, palm fruit and babassu nut has been described. The experimental procedure described in the article starts with a steam distillation for 4-5 hr at 180° C. and a pressure of 2 mm Hg, the distillate being collected in a trap at −80° C. The trap contents are extracted with ether and the residue of the extraction is saponified with a KOH-solution followed by an ether-extraction, after which the acids in the soap are liberated with sulfuric acid and recovered by yet another ether-extraction. After evaporation of the ether the hydroxy acids present are lactonized by dissolving the acid mixture in benzene and refluxing, while distilling of the water liberated from the hydroxy acids. The residual mixture is dissolved in light petroleum and extracted twice with triethanolamine. The triethanolamine soaps were washed with light petroleum and after evaporation of the solvent the residual lactone concentrate was distilled in a cold finger apparatus.

SUMMARY OF THE INVENTION

The present invention relates to a new process for concentrating lactones from a distillate obtained by the distillative deacidification of a fat rich in lauric acid residues, which process is suitable, both from a technical and a commercial viewpoint, for use on a large scale. We have found, namely, that some distillates of fats rich in lauric acid residues, which distillates consist mainly of free fatty acids, contain relatively large amounts, i.e. more than 0.1 wt. % of lactones. We have furthermore found that distillates containing such high amounts of lactones may successfully be used as a starting material in a process for obtaining natural lactones, provided such process involves a fractional distillation.

The process according to the present invention relates therefore to a process for concentrating lactones from a distillate obtained by the distillative deacidification of a fat composition rich in lauric acid residues, said distillate containing at least 0.1 wt. % of lactones having 6-20 carbon atoms, by subjecting the distillate or a fraction thereof to a fractional distillation so as to obtain a fraction containing at least 1 wt. % of lactones having 6-20 carbon atoms. The group of lactones referred to in this application consists of gamma- and delta-lactones, i.e. 4- and 5-alkanolides and 4- and 5-alkenolides having a side chain with a minimal length of 1 carbon atom.

Although it has already been known for more than 20 years that coconut oil contains lactones and despite the fact that distillative deacidification of oils has already been common practice for decades, it has never yet been suggested that in distillates of fats rich in lauric acid residues such high concentrations of lactones may be present that it is commercially and technically attractive to concentrate these lactones from them. In practice, the distillate that is obtained during the refining of vegetable oils is sold as so-called "acid oil", which fetches a price that is even lower than the price of the raw vegetable oil from which the distillate has been obtained.

It has now been found that, by means of a fractional distillation of a steam distillate of fats rich in lauric acid residues, fractions can be obtained which have a lactone content of at least 1 wt. %, preferably at least 1.5 wt. %. Moreover, it is even possible to carry out the fractional distillation in such a manner that for example the $C_8$, $C_{10}$ and $C_{12}$ lactones are recovered mainly in separate fractions.

It is to be understood that the term fractional distillation as used throughout this application does not encompass distillation techniques such as molecular distillation in which no gas-liquid equilibrium is established. In the fractional distillation step employed in the present process such equilibrium is established, i.e. the amount of gas condensing is essentially equal to the amount of liquid evaporating. Preferably the present fractional distillation involves the distillative separation of the starting material into at least three fractions; the possible residue-fraction included. Furthermore the present process preferably is carried out in a continuous or semi-continuous manner at an industrial scale by fractionally distilling the distillate obtained from a distillative deacidification with a throughput of the latter distillate of at least 60 kg/hr.

In a preferred embodiment of the present process the distillate obtained by the distillative deacidification contains at least 0.1 wt. % of lactones having 6-16 carbon atoms, more preferably 8-12 atoms, and the fraction obtained after fractional distillation contains at least 1 wt. % of lactones having 6-16 carbon atoms.

The fat rich in lauric acid residues of which the distillate is used according to the process of the present invention, preferably comprises a lauric fat such as coconut oil, palm kernel oil or babassu oil, more particularly coconut oil or palm kernel oil, coconut oil being most preferred. The fat composition rich in lauric acid residues preferably contains a minimum of 5 wt. %, more particularly at least 30 wt. % of a lauric fat. Throughout this application the terms "fat" and "oil" are considered synonymous and are used interchangeably.

The fat compositions rich in lauric acid residues, of which the distillates are employed in the present process, generally contain more than 20, preferably more than 35 wt. % of lauric acid residues, calculated on the total fatty acid content. By the total fatty acid content is meant here the sum of the content of free fatty acid and the content of fatty acid residues.

BRIEF DESCRIPTION OF THE DRAWING

The drawing is a schematic representation of the yield and the purity of the different fractions obtained during an upgrading procedure described in Example 1.

DETAILED DESCRIPTION OF THE INVENTION

Distillative deacidification of oils is mainly used in order to rid these oils of free fatty acids and other undesired volatile compounds, such as for example malodorous components. This treatment is mostly carried out by heating of the product and passing through it a stream of gas that carries off the volatile components. This gas can be air, but often inert gases are used, such as nitrogen and carbon dioxide, in order to prevent oxidation of the product, while steam is also used as gaseous phase, optionally mixed with other gases.

Steam has as advantage that hydrophilic materials are carried off more rapidly and, moreover, the distillate can be recovered more simply by cooling and condensation of the steam. If deacidification has been carried out with steam, it is advisable first to remove the water before starting distillation.

The distillate, i.e. the volatile components removed from the natural product by the distillative deacidification, possibly mixed with the water originating from the condensed steam, is preferably first subjected to distillation during which a first running is recovered and treated further. This first running has a higher content of lactones than the original distillate, whereafter, by means of fractional distillation of this first running, a virtually quantitative separation of the individual lactones can be obtained.

The end of the first running, and the limits between the different fractions, can best be chosen such that they coincides with the appearance in the distillate of considerable amounts of free fatty acids having a certain number of carbon atoms. It has been found that if this procedure is followed, the lactone that contains just as many carbon atoms as the free fatty acid that is distilled over is then virtually quantitatively distilled over. By recovering a new fraction every time upon the appearance of considerable amounts of free fatty acids, lactones with a different number of carbon atoms are recovered in separate fractions, and thus separated from each other. The free fatty acids in the fractions recovered can be determined by means of, for example, gas chromatography.

A preferred embodiment of the process according to the present invention relates to the subjection of the distillate obtained after distillative deacidification to a further distillation, by which a first running is recovered that contains at least 20 wt. % of fatty acid having 12 carbon atoms, which first running is subsequently subjected to a fractional distillation, from which one or more fractions are recovered containing at least 0.2 wt. % $C_8$ lactone, at least 0.4 wt. % $C_{10}$ lactone or at least 0.4 wt. % $C_{12}$ lactone. In this preferred embodiment thus a fraction of the distillate obtained by distillative deacidification is used as the starting material for the fractional distillation.

The fractional distillation, as carried out in the process according to the invention, preferably takes place under reduced pressure, because in that way better concentrating and separating of the individual lactones are possible.

A further purification of the lactones recovered in a distillate fraction, by the removal especially of free fatty acids, can be obtained by contacting this fraction, which essentially consists of fatty acids and lactones, with an adsorbent on which either the lactones or the fatty acids adsorb, whereafter the non-adsorbed components are eluted and subsequently the adsorbed lactones or fatty acids are desorbed.

It was found that, for example, silica, which is commonly utilized as adsorbent in liquid chromatography, adsorbs lactones better than fatty acids, in the case of a mixture of lactones and fatty acids being dissolved in an apolar solvent and being brought into contact with the silica. Separation of the fatty acids and lactones can subsequently be effected by first eluting the fatty acids with the aid of an apolar solvent and subsequently carrying out desorption of the lactones by elution with a solvent of the proper polarity. Instead of this adsorption-desorption treatment alternatively an additional fractional distillation step may be employed to obtain one or more fractions having a substantially increased lactone content.

An additional advantage of the separation of lactones and fatty acids by means of adsorption-desorption techniques is that not only a lactone fraction is obtained, in which relatively little fatty acid contamination is present, but moreover a relatively pure fatty acid fraction is obtained that can be used for all kinds of purposes. Thus, the present process can be used to upgrade a relatively worthless product, i.e. the distillate, to two valuable fractions, namely a lactone fraction and a fatty acid fraction.

A suitable adsorbent for the adsorption-desorption technique is silica that has preferably been activated by a heat treatment so as to remove essentially all water adsorbed on the silica.

The process according to the invention is preferably used for concentrating the $C_8$–$C_{12}$ lactones, because these have very valuable properties which show up especially well in aroma compositions.

Other aspects of the present invention are a lactone concentrate obtainable by the process according to the present invention and the use of such a lactone concentrate in food products. The optically active natural lactones present in this concentrate are preferably used for flavouring foodstuffs. In particular, the concentrates according to the present invention appear to be suitable for flavouring fat products such as: margarine, low-calorie spreads, frying fat, bakery margarine and cheese products. In addition to this, the concentrates are also suitable for flavouring foodstuffs which contain fruit ingredients, as well as for flavouring imitations of such foodstuffs.

The lactone concentrates obtained by the present process preferably contain at least 30 wt. % of lactones having 8–12 carbon atoms, the remainder of the concentrate, constituting at least 5 wt. % thereof, consisting for at least 60 wt. % of free fatty acids having a chain length of 8–12 carbon atoms. Such lactone concentrates when incorporated in for instance food products appear to impart a more pleasant flavour than synthetic lactone concentrates. It is believed that the present lactone concentrates have a better flavour contribution due to the presence of impurities which have a rounding off effect on the total flavour.

In an even more preferred embodiment the lactone concentrates obtained by the present process and used for flavouring food products contain at least 50 wt. % of lactones having 8-12 carbon, the remainder, constituting at least 10 wt. % of the concentrate, consisting for at least 80 wt. % of free fatty acids having a chain length of 8-12 carbon atoms. Such lactone concentrates appear to have a very balanced aroma contribution and are consequently eminently suitable for use in foodstuffs.

The concentrates according to the present invention are preferably used in combination with other aroma compounds and/or aroma concentrates, because in that way a better attuned aroma can be obtained. If, for example, the lactone concentrates according to the invention are used to impart a butter aroma to spreads, it is advisable that these concentrates be combined with other butter aroma compounds, such as: diacetyl, dimethyl sulphide, methyl ketones, 4-cis-heptenal, etc.

Although it is quite possible for the concentrates obtained according to the present invention to be used as such in foodstuffs, it is naturally also possible to purify the concentrates still further in order to obtain a certain lactone in a degree of purity that can be close to 100%. For certain uses this may be desirable, because the presence of free fatty acids in concentrates can be undesirable.

Still another aspect of the present invention relates to a foodstuff flavoured by the addition of an effective amount of a lactone concentrate obtained by means of the process according to the present invention.

The present invention will now be illustrated by the following examples:

EXAMPLE 1

1) Raw coconut oil (having a fatty acid content of 5 wt. %) was distillatively deacidified in a known manner with the aid of steam at 240° C. and a pressure of 4 mm Hg (5.3*10$^2$ Pa). The distillate obtained (70 tons) contained 18 wt. % oil, and consisted further almost completely of free fatty acids. The delta-lactone composition of the distillate is given in Table A.

2) The distillate recovered was subjected to distillation over a fractionating column having a height of 6.4 m, which column had been packed with refined steel cascade mini rings N° 2. The diameter of the column was 1.4 m. The first running was drawn off as top fraction at a temperature of 175° C. and a pressure of 37 mbar, and had a $C_{12}$ fatty acid content of 73 wt. %. The bottom fraction was drawn off at a temperature of 235° C. and a pressure of 52 mbar. The column had an effectivity of 6 theoretical plates and a reflux ratio of 6. The recovered first running was about 17 wt. % of the original distillate. The lactone composition of the first running is given in Table B.

3) The first running was subjected to a fractional distillation, with a separation on one side into $C_8$ and $C_{10}$ fatty acids and lactones and, on the other side, $C_{12}$ fatty acids and lactones being aimed at. The fractionating column used for the fractional distillation had a height of 10 m and a diameter of 0.22 m. The column was packed with a so-called Sulzer (Trade Name) gauze packing (type BX). The column had an effectivity corresponding with 50 theoretical plates. The pressure at the top of the fractionating column was 20 mbar, the temperature being 144° C., while at the bottom of the column the pressure and temperature were 38 mbar and 192° C., respectively. The reflux ratio of the column at a throughput of the first running of 80.5 kg/h, was found to be 2.8. Both the top fraction and the bottom fraction were drawn off continuously. The lactone composition of the top fraction and the bottom fraction are shown in Table C and Table D, respectively. The top fraction contained further 42.5 wt. % $C_8$ fatty acid and 48.5 wt. % $C_{10}$ fatty acid. The bottom fraction contained 98.2 wt. % $C_{12}$ fatty acid.

4) The above-mentioned bottom fraction was subsequently subjected again to a fractional distillation, use being made of a distillation column as described under 3). The fractionating conditions were chosen such that the temperature at the top of the column was 138° C., at a pressure of 5 mbar, and the temperature at the bottom of the column was 180° C. at a pressure of 14 mbar. The reflux ratio was 177. The composition of the bottom fraction from step 3 which is subjected to the fractional distillation, as well as the composition of the top and bottom fractions obtained during said fractionation are shown in Table E.

5) The top fraction 4) was purified on pilot plant scale by means of adsorption chromatography over an $SiO_2$ column. The column had a height of 50 cm and a diameter of 5 cm. The silica gel used was of the type Hermann M. (ex Gebr. Hermann, Cologne, West Germany). The gel was activated by heating it for 12 hours at 120° C. The weight of the column packing was 0.47 kilogram. The fraction was dissolved in hexane and put on the silica column in an amount corresponding with 0.71 mol delta-lactone per kilogram silica (415 gram). After this had been put on the column, the free fatty acids present were also eluted with hexane, whereafter lactone was subsequently desorbed with an isopropanol/hexane mixture containing 2 wt. % isopropanol.

After the removal of the solvent, a concentrate was obtained having a delta-$C_{12}$-lactone content of 57.9 wt. % and a gamma-$C_{12}$-lactone content of 11.9 wt. %. The yield and the purity of the different fractions during the above-described upgrading procedure are shown schematically in the drawing.

| delta-lactones (% w/w) | Table A | Table B | Table C | Table D |
|---|---|---|---|---|
| $C_8$ | 0.046 | 0.24 | 0.78 | — |
| $C_{10}$ | 0.130 | 0.72 | 1.67 | — |
| $C_{12}$ | 0.054 | 0.25 | <0.1 | 0.3 |

| Table E | bottom fraction 3) | top fraction 4) | bottom fraction 4) |
|---|---|---|---|
| $C_{10}$ fatty acid | 0.10 | 4.7 | — |
| $C_{12}$ fatty acid | 98.0 | 40.2 | 98.8 |
| $C_{12}$ delta lactone | 0.30 | 12.9 | 0.001 |

What is claimed is:

1. Process for concentrating lactones from a distillate containing at least 0.1 wt. % of lactones having 6-20 carbon atoms and obtained by distillative deacidification of a fat composition rich in lauric acid residues, the process comprising subjecting the distillate or a fraction thereof to a fractional distillation so as to obtain a fraction containing at least 1 wt. % of lactones having 6-20 carbon atoms, in which process the fraction of the distillate is subjected to the fractional distillation comprising the steps of:
   (a) subjecting the distillate obtained after the distillative deacidification to a first distillation;
   (b) recovering the fraction which is a first running that contains at least 20 wt. % of fatty acid having 12 carbon atoms;

(c) subjecting the first running to the fractional distillation; and (d) recovering one or more fractions containing at least 0.2 wt. % $C_8$ lactone, at least 0.4 wt. % $C_{10}$ lactone or at least 0.4 wt. % $C_{12}$ lactone.

2. Process according to claim 1, wherein the fat composition rich in lauric acid residues contains at least 20 wt. % of lauric acid residues, calculated on the total fatty acid content.

3. Process according to claim 2, wherein the fat composition contains at least 30 wt. % of lauric fat.

4. Process according to claim 1, wherein the process is carried out in a continuous or semi-continuous manner at an industrial scale by fractionally distilling the distillate obtained from a distillative deacidification at a throughput of at least 60 kg/hr.

5. Process according to claim 1, wherein the fraction obtained by fractional distillation comprises at least 1 wt. % of lactones having 6-16 carbon atoms.

6. Process for concentrating lactones from a distillate containing at least 0.1 wt. % of lactones having 6-20 carbon atoms and obtained by distillative deacidification of a fat composition rich in lauric acid residues, the process comprising subjecting the distillate or a fraction thereof to a fractional distillation so as to obtain a fraction containing at least 1 wt. % of lactones having 6-20 carbon atoms, the process comprising the additional steps of:

(a) contacting the fraction obtained after fractional distillation, which fraction essentially consists of fatty acids and lactones, with an adsorbent on which the lactones adsorb;

(b) eluting the non-adsorbed components of the fraction; and (c) and subsequently desorbing the adsorbed lactones.

7. Process according to claim 6, wherein the lactone concentrate obtained contains at least 30 wt. % of lactones having 8-12 carbon atoms, the remainder of the concentrate, constituting at least 5 wt. % thereof, consisting for at least 60 wt. % of free fatty acids having a chain length of 8-12 carbon atoms.

8. Process for concentrating lactones from a distillate containing at least 0.1 wt. % of lactones having 6-20 carbon atoms and obtained by distillative deacidification of a fat composition rich in lauric acid residues, the process comprising subjecting the distillate or a fraction thereof to a fractional distillation so as to obtain a fraction containing at least 1 wt. % of lactones having 6-20 carbon atoms, the process comprising the additional steps of:

(a) contacting the fraction obtained after fractional distillation, which fraction essentially consists of fatty acids and lactones, with an adsorbent on which the fatty acids adsorb;

(b) eluting the non-adsorbed components of the fraction; and (c) and subsequently desorbing the adsorbed fatty acids.

* * * * *